Figure 1:
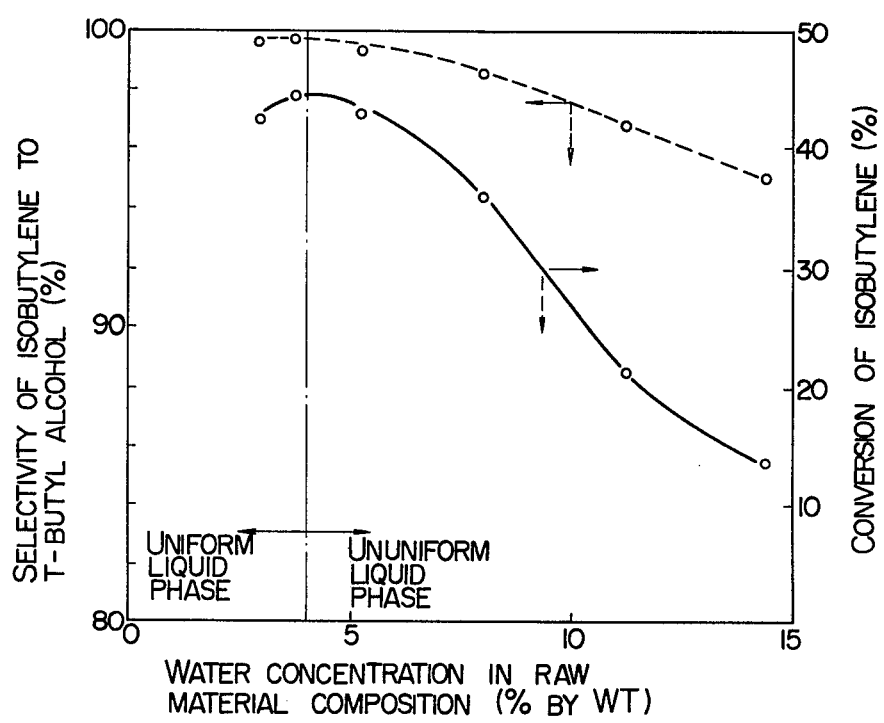

United States Patent [19]

Sada et al.

[11] 4,307,257

[45] Dec. 22, 1981

[54] PROCESS FOR PRODUCTION OF TERTIARY BUTYL ALCOHOL

[75] Inventors: Masao Sada, Nara; Michio Kato, Niihama; Yoshihide Mori, Niihama; Michikazu Sano, Niihama, all of Japan

[73] Assignee: Sumitomo Chemical Company, Limited, Osaka, Japan

[21] Appl. No.: 161,895

[22] Filed: Jun. 23, 1980

[30] Foreign Application Priority Data

Jul. 5, 1979 [JP] Japan .................................. 54/85612

[51] Int. Cl.$^3$ ............................................. C07C 29/04
[52] U.S. Cl. ..................................................... 568/899
[58] Field of Search ......................................... 568/899

[56] References Cited

U.S. PATENT DOCUMENTS

| 3,328,471 | 6/1967 | Kronig et al. | 568/899 |
| 4,087,471 | 5/1978 | Bowman et al. | 568/899 |
| 4,182,920 | 1/1980 | Giles et al. | 568/899 |

FOREIGN PATENT DOCUMENTS

| 702949 | 2/1965 | Canada | 568/899 |
| 50-137906 | 11/1975 | Japan | 568/899 |

OTHER PUBLICATIONS

Odioso et al., "I. & E. C.", vol. 53, No. 3, pp. 209–211, (1961).

Primary Examiner—Joseph E. Evans
Attorney, Agent, or Firm—Stevens, Davis, Miller & Mosher

[57] ABSTRACT

An aqueous high concentration solution of tert-butyl alcohol can be produced with high conversion and high selectivity by using a material composition having special proportions of tert-butyl alcohol, water and isobutylene or an isobutylene-containing hydrocarbon mixture and reacting isobutylene with water in the presence of a cation exchange resin having sulfonic acid groups preferably in multi-stage reactors and separating inert hydrocarbons and unreacted isobutylene from the reaction solution in a distillation column.

7 Claims, 4 Drawing Figures

PROCESS FOR PRODUCTION OF TERTIARY BUTYL ALCOHOL

This invention relates to a process for producing tert-butyl alcohol by reacting isobutylene with water in the presence of an acidic cation exchange resin.

Tert-Butyl alcohol can be added to gasoline to improve antiknock characteristics and anti-freezing characteristics or can be used not only as a starting material for producing high purity isobutylene when dehydrated but also as a starting material for producing methyl methacrylate by a vapor phase catalytic oxidation process by itself or in the form of aqueous solution thereof.

Processes for producing tert-butyl alcohol by reacting isobutylene or hydrocarbons containing isobutylene with water in the presence of various catalysts have been known and disclosed in many patent specifications. For example, there are disclosed a process comprising using a catalyst obtained by impregnating a solid carrier with orthophosphoric acid or using an aqueous solution of 40 to 70% by weight of sulfuric acid in Published Examined Japanese patent application No. 23524/72, processes comprising using heteropoly acid such as silicotungstic acid or its heavy metal salts supported on proper carriers as catalyst in Published Examined Japanese patent application Nos. 2487/75, 36203/74, 36204/74, etc., processes comprising using an aqueous solution of ferric sulfate or an aqueous solution of antimony chloride, etc. in Published Examined Japanese patent application Nos. 7125/74, 14765/70, 18088/66, etc.

But the process comprising using the aqueous sulfuric acid solution has many defects in that when relatively low acid concentrations are employed so as to lessen corrosion of the apparatus, the activity is lowered, while high acid concentrations are employed, there not only arises a problem of corrosion of the apparatus but also increase side reactions such as polymerization of olefins and the like. In the case of vapor phase hydration reactions using phosphoric acid series and heteropoly acid series catalysts, there are defects in that the equilibrium conversion is low since the reaction temperature is 150° to 300° C. and the reaction is exothermic at such a temperature, and in order to enhance the equilibrium conversion, it is necessary to use water in a large excess to the amounts of olefins but the large excess of water may dissolve the effective component of the catalyst in the reaction products when the reaction is carried out for a long period of time. Further, the process of using the aqueous solution of hydrochlorides or sulfates of metals such as iron, antimony or the like, as catalyst requires a further step of removing the metal hydrochlorides or metal sulfates, so that there arise various problems such as removal of heavy metals in waste water and the like, and thus said processes are not suitable for industrial production.

On the other hand, the reaction of isobutylene in a so-called spent BB fraction with one molecule of water in the presence of a cation exchange resin having sulfonic acid groups to produce continuously tert-butyl alcohol is known, for example, by Ind. Eng. Chem. vol. 53, No.3, 209–211 (1961), but the conversion of isobutylene in such a case is as low as about 30%.

Processes comprising adding third organic substances such as organic acids and alcohols to the reaction system are disclosed in Published Unexamined Japanese patent application Nos. 126603/75 and 137906/75. But when a third organic substance such as acetic acid, methanol, or the like other than tert-butyl alcohol is added to the reaction system, there are defects in that it is necessary to separate and recover the third organic substance in some steps in the process and the yield is decreased due to the reaction of the third organic substance with isobutylene to give by-products such as esters, ethers, and the like other than the desired product.

Further a process comprising adding tert-butyl alcohol, which is the desired reaction product, and using an acidic ion exchange resin as a catalyst is disclosed in Published Unexamined Japanese patent application No. 137906/75. According to this Patent Application, there is a description that 10 to 500 moles of alcohols (including tert-butyl alcohol) per 100 moles of water are added. This range of material composition includes those almost unsuitable for producing tert-butyl alcohol, i.e. in multi-components systems comprising tert-butyl alcohol, water and an isobutylene-containing hydrocarbon mixture, there is a composition range of a so-called ununiform phase comprising oil phase and aqueous phase, a composition range wherein water and tert-butyl alcohol are contained in very high concentration and the hydrocarbon mixture is contained in low concentration, and a composition range of a uniform oil phase wherein the hydrocarbon mixture is contained in very high concentration and mutual solubility for water is very small. Further, since a strongly acidic cation exchange resin generally has very strong affinity for water and remarkably reduces the reaction rate of isobutylene by inhibiting adsorption of isobutylene to be reacted when an excessively large amount of water is present on the surface of the catalyst, it is very disadvantageous from the viewpoint of efficiency of catalyst to carry out the reaction by using a composition containing a large amount of water. In addition, to use a material composition containing water and tert-butyl alcohol in high concentrations disadvantageously lowers the equilibrium conversion due to high concentration of tert-butyl alcohol which belongs to a product system, since the reaction of isobutylene with water to produce tert-butyl alcohol is a reversible reaction. In the range of material composition wherein the concentration of hydrocarbon mixture is high and mutual solubility for water is very small, the positive reaction rate in the reversible reaction of isobutylene with water to produce tert-butyl alcohol is remarkably lowered with a decrease of water concentration while by-products such as dimer of isobutylene and the like are easily produced due to higher isobutylene concentration, so that it is very disadvantageous to select the starting material composition having such a range. That is, it is impossible to suppress side reactions and to accelerate the reaction rate by adding only tert-butyl alcohol to the reaction system of isobutylene or a hydrocarbon mixture containing isobutylene with water as taught by the said Japanese Patent Application.

It is an object of this invention to provide a process for producing tert-butyl alcohol industrially advantageously by the reaction of isobutylene with water.

This invention provides a process for producing tert-butyl alcohol which comprises contacting isobutylene or a $C_3$ to $C_5$ hydrocarbon mixture comprising $C_4$ hydrocarbons as major components with water in the presence of a sulfonic acid group-containing cation exchange resin, the composition in a reaction zone of tert-butyl alcohol, water and isobutylene or the hydrocarbon mixture being as defined by closed area of A-B-C-D-E-F-G-H-A in the accompanying triangular diagram, wherein the points A to H have the following compositions in percents by weight:

|   | tert-butyl alcohol | water | isobutylene or hydrocarbon mixture |
|---|---|---|---|
| A | 55.3 | 31.0 | 13.7 |
| B | 52.5 | 20.2 | 27.3 |
| C | 41.0 | 14.5 | 44.5 |
| D | 9.8 | 10.2 | 80.0 |
| E | 24.0 | 0.3 | 75.7 |
| F | 53.8 | 1.0 | 45.2 |
| G | 70.5 | 1.7 | 27.8 |
| H | 78.0 | 2.6 | 19.4 |

In the present invention, "the $C_3$ to $C_5$ hydrocarbon mixture comprising $C_4$ hydrocarbons as the major components" means a so-called spent BB fraction, which is obtainable by pyrolysis of naphtha to obtain a so-called BB fraction (butane-butene stream), followed by extraction to recover butadiene, and is hereinafter referred to as "the hydrocarbon mixture" for brevity.

Figure 2:
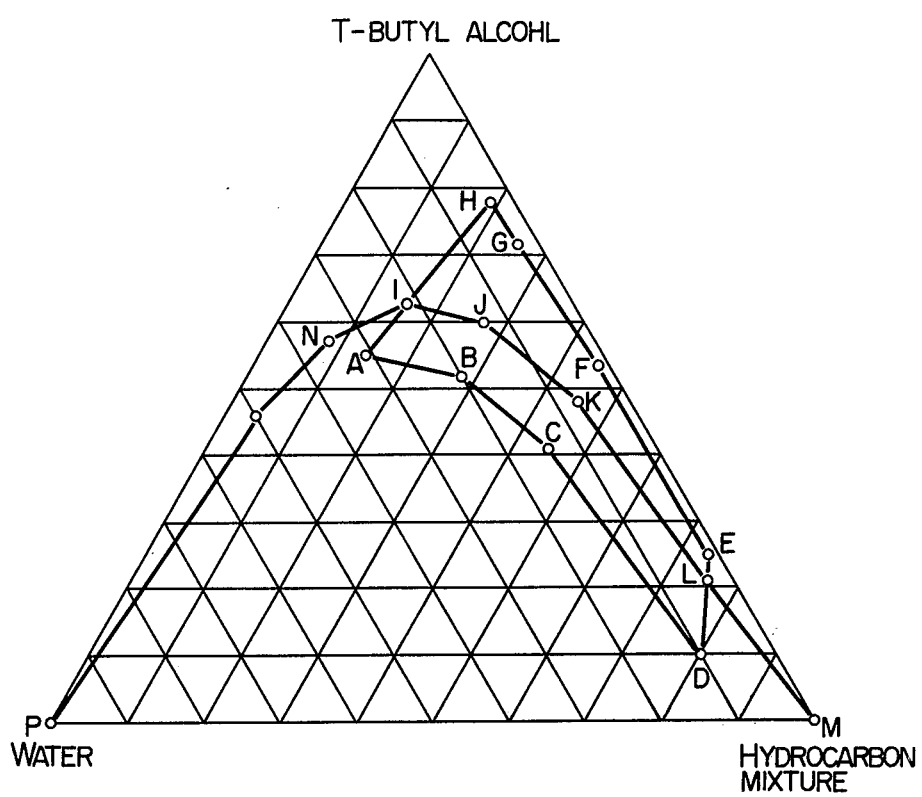
Figure 3:
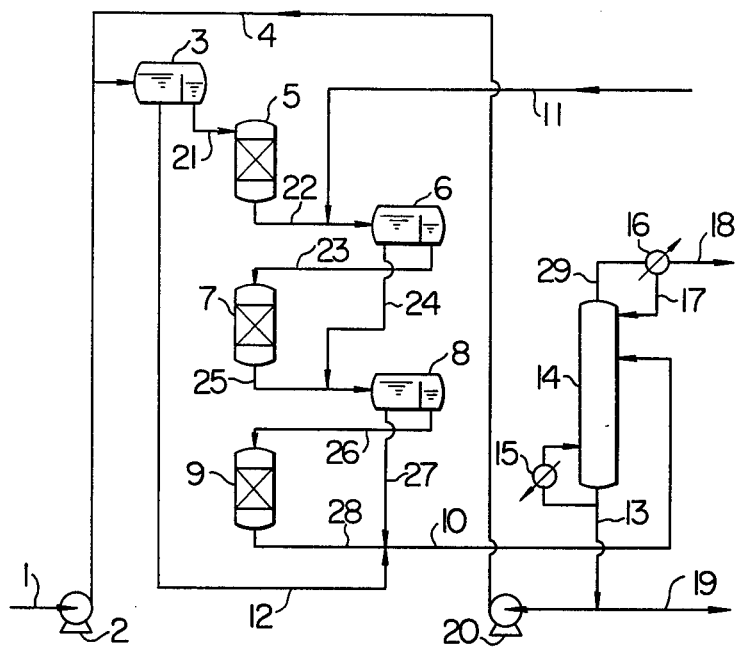
Figure 4:
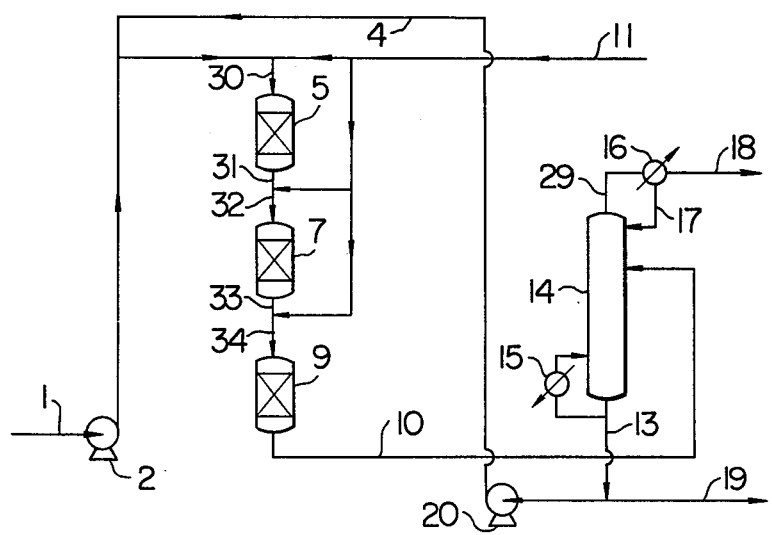

In the attached drawings,

FIG. 1 is a graph showing relationship between the selectivity of isobutylene to tert-butyl alcohol or conversion of isobutylene and the water content in the material composition, provided that the hydrocarbon content is fixed, FIG. 2 is a triangular diagram showing usable and preferable ranges of three component system of tert-butyl alcohol, water and isobutylene or the hydrocarbon mixture, and FIGS. 3 and 4 are flow sheets showing preferable embodiments of this invention.

The present invention has been attained through the knowledge obtained by conducting the following experiments. The reaction of isobutylene and water was carried out under the following conditions by varying concentrations of tert-butyl alcohol and water in the material composition in a reaction zone, whereas the concentration of the hydrocarbon mixture (isobutylene 45.0% by weight, butanes 12.8% by weight, butenes 40.2% by weight, and others 2% by weight) was fixed at 60% by weight.

| Reaction temperature | 70° C. |
|---|---|
| Reaction pressure | 15 kg/cm$^2$ |
| Catalyst (single stage fixed bed) | Duolite ES-26 (Diamond Shamrock Co.) 220 ml |
| Volume of reactor | 300 ml |

The results were as shown in FIG. 1. In FIG. 1, the solid line shows conversion of isobutylene and the dotted line shows selectivity of isobutylene to tert-butyl alcohol. As shown in FIG. 1, the material composition having compositions near the boundary of the aqueous phase and the oil phase has excellent values in reaction rate and selectivity.

Further, experiments were carried out varying the content of isobutylene or the hydrocarbon mixture in the material composition, and as a result it was found that an area closed by the straight lines connecting each point, A, B, C, D, E, F, G and H, as shown in FIG. 2, is optimum in the production of tert-butyl alcohol with industrial advantages. In FIG. 2, the solid line obtained by connecting individual points of P, O, N, I, J, K, L and M shows a boundary line between a uniform liquid phase region and an ununiform liquid phase region and the upper portion above the boundary line is the uniform liquid phase region and the lower portion below the boundary line is the ununiform liquid phase region. Individual points in FIG. 2 have the composition as listed in Table 1.

TABLE 1

| Point | tert-Butyl alcohol (% by weight) | Water (% by weight) | Isobutylene or hydrocarbon mixture (% by weight) |
|---|---|---|---|
| A | 55.3 | 31.0 | 13.7 |
| B | 52.5 | 20.2 | 27.3 |
| C | 41.0 | 14.5 | 44.5 |
| D | 9.8 | 10.2 | 80.0 |
| E | 24.0 | 0.3 | 75.7 |
| F | 53.8 | 1.0 | 45.2 |
| G | 70.5 | 1.7 | 27.8 |
| H | 78.0 | 2.6 | 19.4 |
| I | 62.5 | 22.0 | 15.5 |
| J | 59.8 | 12.5 | 27.7 |
| K | 48.5 | 6.7 | 44.8 |
| L | 21.6 | 2.2 | 76.2 |
| M | 0 | 0 | 100 |
| N | 57.5 | 35.0 | 7.5 |
| O | 46.5 | 49.8 | 3.7 |
| P | 0 | 100 | 0 |

The present invention is illustrated in more detail below.

As to the cation exchange resins usable in the present invention, there is no limitation for the kind thereof. For example, they can be produced by treating a resin such as styrene resins, acryl resins, phenol resins and the like with sulfuric acid. Of these, there are preferably usuable strongly acidic cation exchange resins of styrene series which can be produced by polymerization of styrene using divinylbenzene as a cross-linking agent and then treating the resulting resin with sulfuric acid to introduce sulfonic acid groups. More preferred are those which are porous cation exchange resins having macro pores and extremely large surface area. The cation exchange resins of this kind commercially available include, for example, Amberlite 200C (Rohm & Haas Co.), Duolite ES-26 (Diamond Shamrock Co.) and the like.

As to the material composition in the reaction zone, when the material composition has a larger content of tert-butyl alcohol than the line AH and a lower content of hydrocarbon mixture than the line AH, the equilibrium conversion is lowered due to too much amount of tert-butyl alcohol and at the same time the hydrocarbon mixture content becomes smaller and thus the isobutylene content becomes lower, which results in reducing the reaction rate.

When the material composition is in the area under the ununiform liquid phase having a larger water content than the line drawn between the points A, B, C, and D in FIG. 2, side reactions such as dimerization of isobutylene, and the like take place more often and the reaction rate is undesirably reduced.

When the material composition has a smaller content of tert-butyl alcohol than the line DE and a higher content of hydrocarbon mixture than the line DE, side reactions such as dimerization of isobutylene easily take place undesirably.

When the material composition is in the area having a smaller water content than the line drawn between the points E, F, G, and H in FIG. 2, the reaction rate is undesirably reduced due to the small content of water which is a raw material.

As explained above, the material composition should have the composition falling within the closed area A-B-C-D-E-F-G-H-A. When tert-butyl alcohol produced having higher purity is required, the material composition within the closed area I-J-K-L-E-F-G-H-I is preferably used. Further, considering the reaction rate and operational efficiency, the starting material composition for feeding to the inlet of the reactor preferably has the composition on the boundary line between the uniform liquid phase and the ununiform liquid phase, i.e. on the line drawn between the points I, J, K and L.

Even if the reaction is carried out in the area of compositions as mentioned above, since the equilibrium conversion is limited to 40 to 60% in a temperature range preferable for industrial production due to the limitation derived from a thermodynamic equilibrium theory, it is difficult in principle to attain the conversion sufficient for industrial production in one step in a single-stage reactor. Further, since there is a tendency to lower the reaction rate due to lowering of the water concentration derived from the consumption of water by the reaction when the reaction is near to the equilibrium conversion, it is preferable to use multi-stage reactors in series having 2 to 5 stages.

Any types of reactors, either continuous type or batch type, conventionally used in the solid-liquid contact reactions can be used in the process of the present invention. When continuous flow type reactors are used, fixed bed type is most generally used but not limited thereto. When fixed bed flow type reactors are used, either upward flow or downward flow of a liquid may be possible, and in general the downward flow is preferable.

When multi-stage reactors are used, water is continuously supplied at each entrance of each reaction stage so that the material composition becomes that defined above at each reaction zone. More preferably, each liquid-liquid contact apparatus such as a stirring tank, a decanter, etc. may be set at each entrance of each reaction stage and water is saturated at the oil phase side by separation on standing.

As methods for supplying water at each entrance of each reaction stage, in the case of using a starting material containing only the hydrocarbon mixture containing isobutylene without containing tert-butyl alcohol at the inlet of first-stage, it is preferable to use an aqueous solution of tert-butyl alcohol in high concentration in order to enhance the mutual solubility for water and to contact the two solutions so as to supply water. In the case of adding tert-butyl alcohol to a starting material of hydrocarbon mixture containing isobutylene previously, water alone can be used for supply. Since there is contained a sufficient amount of tert-butyl alcohol in the material composition after the second-stage or later, it is better to use water alone or a dilute aqueous solution of tert-butyl alcohol.

When multi-stage reactors are used, separation apparatus such as extractors, distillation columns, etc. may be set other than the reacting water supply liquid-liquid contact apparatus mentioned above between each stage reactor so as to control the composition of reaction solution for the next stage reactor.

When the reaction temperature is too high, side reactions may take place, whereas too low reaction temperature makes the reaction rate slow, so that the reaction is carried out at 30° to 110° C., preferably 50° to 90° C. When multi-stage reactors are used, different reaction temperatures may be used at individual stages within the range mentioned above.

As to the reaction pressure, a pressure equal to or higher than the saturated vapor pressure of the hydrocarbon mixture at the reaction temperature employed and preferably 40 kg/cm$^2$ or less may be used. Preferred is a pressure of the vapor pressure of hydrocarbon mixture plus 2 to 8 kg/cm$^2$, thereby causing no evaporation in the reactor.

A total conversion of isobutylene depends on the amount of catalyst used under the reaction conditions and the number of stages of the reactors, and the conversion of isobutylene is preferably controlled in the range of 50 to 95% from economical point of view.

The reaction product solution obtained from the final-stage reactor is lead to a distillation column operated under a pressure of equal to or lower than the pressure of the reactor but equal to or higher than 1 kg/cm$^2$. In this distillation column, inert hydrocarbons contained in the hydrocarbon mixture and unreacted isobutylene are separated and removed to directly give an aqueous solution of highly concentrated tert-butyl alcohol. If the pressure of the distillation column is higher than the pressure of the reactor, the temperature of heating medium of the reboiler becomes higher; this is disadvantageous from economical point of view. On the other hand, if the pressure is lower than 1 kg/cm$^2$, it is difficult to condense the separated inert hydrocarbons and unreacted isobutylene by using a conventional industrial cooling medium; this is not preferable.

The distillation can usually be carried out by using one distillation column, and various means including side cut, complex distillation columns, etc. can be used. This invention is not limited by such distillation methods. Further, any distillation columns conventionally used such as packed columns, perforated plate columns, plate columns, and the like can be used. This invention is not limited by types of distillation columns.

The concentration of tert-butyl alcohol in the aqueous solution separated from the distillation column can be controlled by determining the supplying amount of water to the distillation column depending on purposes of the use and considering azeotropic relation between tert-butyl alcohol and water. But the concentration of 30% by weight or more, preferably 50% by weight or more, of tert-butyl alcohol in the aqueous solution is usually used.

Needless to say, the thus obtained aqueous solution of highly concentrated tert-butyl alcohol can be used as an aqueous tert-butyl alcohol solution for feeding so as to mix with the hydrocarbon mixture at the entrance of the reactor.

This invention is illustrated in detail referring to FIG. 3 wherein three-stage reactors are used, but this is only one example of this invention which is not limited to such an example.

In FIG. 3, the hydrocarbon mixture is passed through line 1 and compressed by a pump 2 and mixed with tert-butyl alcohol which is passed through line 4. Thereafter, the resulting mixed solution is passed to a separator 3 wherein it is separated into two liquids, one of which is rich in the hydrocarbon mixture (hereinafter referred to as oil phase) and the other of which is rich in water (hereinafter referred to as aqueous phase). The oil phase is passed to a first-stage reactor 5 packed with a cation exchange resin as catalyst. The reaction solution is taken out of the first-stage reactor 5 and reaction water required is supplied to the reaction solution through line 11 and the resulting mixed solution is passed to a separator 6 wherein the mixture is separated to an oil phase and an aqueous phase. Only the oil phase saturated with water is passed to a second-stage reactor 7 packed with a cation exchange resin.

To the reaction solution taken out of the second-stage reactor 7, the liquid of aqueous phase separated in the separator 6 passed through line 24 is added and passed to a separator 8 wherein an oil phase and an aqueous phase are separated. The oil phase saturated with water only is passed to a third-stage reactor 9 packed with a cation exchange resin. The reaction solution taken out of the third-stage reactor 9 through line 28 is mixed with the excess aqueous phase separated in the separator 8 through line 27 and the resulting mixed solution is passed to a distillation column 14 through line 10.

From line 29 at the top of the distillation column, inert hydrocarbons, unreacted isobutylene, tert-butyl alcohol and water are taken out as vapors and condensed in a condenser 16 and refluxed through line 17 while the distilate is taken out through line 18. A portion of the bottoms taken out of the bottom of distillation column 14 through line 13 is returned to the separator 3 by a pump 20 through line 4 as a reacting water feeding liquid to the first-stage reactor 5 and the rest of the bottoms is taken out through line 19 as a highly concentrated aqueous solution of tert-butyl alcohol, or the product.

This invention is illustrated by way of the following Examples but not limited thereto. In the following Examples, numerals as to lines and devices are the same as shown in FIGS. 3 and 4 and analysis is conducted by gas chromatography.

EXAMPLES 1-4,

Comparative Examples 1-3

A cylinder type reactor having an inner volume of 1 liter made of stainless steel was packed with 0.7 liter of Duolite ES-26 (Diamond Shamrock Co.) as catalyst. To the reactor, a starting material composition having the composition as shown in Table 2 was supplied via a mixing tank and the reaction was carried out at a temperature of 70° C. under a pressure of 16 kg/cm$^2$.

The reaction mixture taken out of the reactor was analyzed to give conversion rate of isobutylene and selectivity of isobutylene to tert-butyl alcohol.

The results are as shown in Table 2.

TABLE 2

| Example No. | Flow rate of starting materials (kg/hr) | | | Conversion rate of isobutylene (kg/hr) | Selectivity to tert-butyl alcohol (%) |
| --- | --- | --- | --- | --- | --- |
| | Hydrocarbon mixture* | Water | tert-Butyl alcohol | | |
| Example 1 | 0.426 | 0.324 | 0.955 | 0.125 | 99.6 |
| Example 2 | 0.417 | 0.217 | 1.034 | 0.133 | 99.8 |
| Example 3 | 0.835 | 0.057 | 0.283 | 0.141 | 97.3 |
| Example 4 | 0.842 | 0.038 | 0.316 | 0.114 | 99.0 |
| Comparative Example 1 | 0.451 | 0.632 | 0.722 | 0.065 | 94.32 |
| Comparative Example 2 | 0.830 | 0.172 | 0.172 | 0.068 | 90.2 |
| Comparative Example 3 | 0.991 | 0.051 | 0.051 | 0.145 | 85.4 |

(Note)
*Composition of hydrocarbon mixture:
isobutylene 45.0% by weight
butanes 12.8% by weight
butenes 40.8% by weight
others 2% by weight

EXAMPLE 5

Synthesis of tert-butyl alcohol was carried out according to the flow sheet shown in FIG. 3 using the same hydrocarbon mixture as used in Example 1 as a starting material for feeding through line 1. Individual devices were operated under the conditions as shown in Table 3. Compositions and flow rates at individual lines in the flow sheet of FIG. 3 were as shown in Table 4.

TABLE 3

| | Reactors (5), (7) and (9) | Separators (3), (6) and (8) | Distillation column |
| --- | --- | --- | --- |
| Type | Fixed bed Inner diameter 16 mm Length 1400 mm | Decanter Inner volume 2 l | Perforated plate column 4 steps |
| Material | SUS 316L | SUS 304 | SUS 304 |
| Packing material | Catalyst Duolite ES-26 Catalyst volume of each reactor 220 ml | — | — |
| Operational pressure | Each reactor 16 kg/cm$^2$ | Each separator 16 kg/cm$^2$ | 3.5 kg/cm$^2$ |
| Operational temperature | Reactor (5) 70° C. Reactor (7) 70° C. Reactor (9) 60° C. | Separator (3) 70° C. Separator (6) 70° , C. Separator (8) 60° , C. | 120° C.-70° C. |

TABLE 3-continued

|  | Reactors (5), (7) and (9) | Separators (3), (6) and (8) | Distillation column |
|---|---|---|---|
| Reflux ratio | — | — | 1.6 |

TABLE 4

| Composition and flow rate | Numerals of lines | | | | | | | | |
|---|---|---|---|---|---|---|---|---|---|
| | 1 | 4 | 10 | 11 | 18 | 19 | 21 | 23 | 26 |
| Isobutylene (% by wt.) | 45.0 | — | 3.2 | — | 10.3 | — | 25.4 | 15.2 | 6.7 |
| Hydrocarbon mixture other than isobutylene (% by wt.) | 55.0 | — | 28.1 | — | 89.6 | — | 31.0 | 29.8 | 28.1 |
| tert-Butyl alcohol (% by wt.) | — | 89.6 | 61.5 | — | 0.07 | 89.6 | 39.1 | 48.8 | 56.9 |
| Water (% by wt.) | — | 10.4 | 7.2 | 100.0 | 0.03 | 10.4 | 4.5 | 6.2 | 8.3 |
| Dimer of isobutylene (% by wt.) | — | trace | trace | — | — | trace | trace | trace | trace |
| Trimer of isobutylene (% by wt.) | — | — | — | — | — | — | — | — | — |
| sec-Butyl alcohol (% by wt.) | — | — | — | — | — | — | — | — | — |
| Flow rate (g/hr) | 332 | 255 | 646 | 61 | 203 | 188 | 585 | 609 | 646 |

EXAMPLE 6

Synthesis of tert-butyl alcohol was carried out according to the flow sheet shown in FIG. 4 using the same hydrocarbon mixture as used in Example 1 as a starting material for feeding through line 1. Individual devices were operated under the conditions as shown in Table 5. Compositions and flow rates at individual lines in the flow sheet of FIG. 4 were as shown in Table 6.

TABLE 5

|  | Reactors (5), (7) and (9) | Distillation column |
|---|---|---|
| Type | Fixed bed Inner diameter 27 mm Length 1400 mm | Perforated plate column 4 steps |
| Material | SUS 316L | SUS 304 |
| Packing material | Catalyst: Duolite ES-26 Catalyst volume of each reactor: 0.7 l. | — |
| Operational pressure | Each reactor: 16 kg/cm² | 3.5 kg/cm² |
| Operational temperature | Each reactor: 70° C. | 120°–70° C. |
| Reflux ratio | — | 1.6 |

TABLE 6

| Composition and flow rate | Numerals of lines | | | | | | | |
|---|---|---|---|---|---|---|---|---|
| | 1 | 4 | 10 | 18 | 19 | 30 | 32 | 34 |
| Isobutylene (% by wt.) | 45.0 | — | 3.24 | 8.6 | — | 32.0 | 18.8 | 7.04 |
| Hydrocarbon mixture other than isobutylene (% by wt.) | 55.0 | — | 34.5 | 91.3 | — | 39.0 | 36.5 | 34.5 |
| tert-Butyl alcohol (% by wt.) | — | 86.5 | 53.8 | 0.07 | 86.5 | 24.0 | 36.9 | 48.8 |
| Water (% by wt.) | — | 12.6 | 7.9 | 0.03 | 12.6 | 4.75 | 7.4 | 9.1 |
| Dimer of isobutylene (% by wt.) | — | 0.9 | 0.56 | trace | 0.9 | 0.25 | 0.4 | 0.56 |
| Trimer of isobutylene (% by wt.) | — | — | — | — | — | — | — | — |
| sec-Butyl alcohol (% by wt.) | — | — | — | — | — | — | — | — |
| Flow rate (g/hr) | 835 | 327 | 1329 | 502 | 500 | 1177 | 1257 | 1329 |

|  | tert-butyl alcohol | water | isobutylene or hydrocarbon mixture |
|---|---|---|---|
| I | 62.5 | 22.0 | 15.5 |
| J | 59.8 | 12.5 | 27.7 |
| K | 48.5 | 6.7 | 44.8 |
| L | 21.6 | 2.2 | 76.2 |
| E | 24.0 | 0.3 | 75.7 |
| F | 53.8 | 1.0 | 45.2 |
| G | 70.5 | 1.7 | 27.8 |
| H | 78.0 | 2.6 | 19.4 |

What is claimed is:

1. A process for producing tert-butyl alcohol, comprising contacting isobutylene or a C₃ to C₅ hydrocarbon mixture comprising C₄ hydrocarbons as the major component, with water in the presence of a sulfonic acid group-containing cation exchange resin, wherein the composition in a reaction zone of tert-butyl alcohol, water and isobutylene or the hydrocarbon mixture is a uniform liquid composition within the closed area I-J-K-L-E-F-G-H-I in the accompanying triangular diagram wherein the points I to H have the following compositions in percents by weight:

2. A process according to claim 1, wherein the reaction zone is multi-stage reactors in series.

3. A process according to claim 2, wherein the multi-stage reactors in series have 2 to 5 stages.

4. A process according to claim 2, wherein the starting material composition for feeding to each inlet of each stage reactor has a composition on the line obtained by drawing points of I, J, K and L in the accompanying triangular diagram and saturated with water, these points having the following compositions in percents by weight:

|  | tert-butyl alcohol | water | isobutylene or hydrocarbon mixture |
|---|---|---|---|
| I | 62.5 | 22.0 | 15.5 |
| J | 59.8 | 12.5 | 27.7 |
| K | 48.5 | 6.7 | 44.8 |
| L | 21.6 | 2.2 | 76.2 |

5. A process according to claim 1, wherein the contacting is carried out at a temperature of 50° to 90° C.

6. A process according to claim 1, wherein the contacting is carried out at a pressure equal to or higher than the saturated vapor pressure of the hydrocarbon mixture at the reaction temperature but not higher than 40 kg/cm².

7. A process according to claim 2, wherein a total conversion of isobutylene at the outlet of the final-stage reactor of multi-stage reactors in series is 50 to 95% by mole.

* * * * *